United States Patent
Zou et al.

(10) Patent No.: US 7,912,180 B2
(45) Date of Patent: Mar. 22, 2011

(54) SCATTERED RADIATION CORRECTION METHOD AND SCATTERED RADIATION CORRECTION APPARATUS

(75) Inventors: Yu Zou, Naperville, IL (US); Michael D. Silver, Northbrook, IL (US); Satoru Ohishi, Otawara (JP); Kozo Sato, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 12/388,947

(22) Filed: Feb. 19, 2009

(65) Prior Publication Data

US 2010/0208870 A1     Aug. 19, 2010

(51) Int. Cl.
*G01N 23/201*     (2006.01)
*G01N 23/00*     (2006.01)

(52) U.S. Cl. ............................. 378/87; 378/7

(58) Field of Classification Search .......... 378/4, 6, 378/7, 9, 19, 70, 86–90
See application file for complete search history.

(56) References Cited

U.S. PATENT DOCUMENTS

| | | | |
|---|---|---|---|
| 4,656,650 A | | 4/1987 | Kikuchi et al. |
| 6,163,589 A | * | 12/2000 | Vartanian .................. 378/7 |

FOREIGN PATENT DOCUMENTS

JP     2-56877     12/1990

* cited by examiner

*Primary Examiner* — Irakli Kiknadze
(74) *Attorney, Agent, or Firm* — Oblon, Spivak, McCelland, Maier, & Neustadt, L.L.P.

(57) ABSTRACT

Scattered radiation is estimated by using a reduced image generated from a projection image, and the scattered radiation image of the projection image is acquired by enlargement processing. The scattered radiation correction of the projection image is executed by subtracting the obtained scattered radiation image from the projection image. In addition, when a primary X-ray image and a scattered radiation image in each projection direction are to be obtained by sequential approximation calculation, a primary X-ray image which has already been identified in an adjacent projection direction is used as a first estimated value (initially set value) in next sequential calculation.

6 Claims, 9 Drawing Sheets

SCATTERED RADIATION CORRECTION METHOD AND SCATTERED RADIATION CORRECTION APPARATUS

BACKGROUND OF THE INVENTION

1. Field of the Invention

The present invention relates to a scattered radiation correction method and a scattered radiation correction method which are used on an X-ray diagnostic apparatus which can execute CT-like imaging, an X-ray computed tomographic apparatus or the like.

2. Description of the Related Art

In general, an X-ray projection image contains many scattered radiation components. This scattered radiation greatly degrades the accuracy of a CT value in three-dimensional imaging using a two-dimensional detector. A two-dimensional detector like a flat panel detector used in an X-ray diagnostic apparatus uses a scattered radiation removing grid to suppress scattered radiation. This effect, however, is much inferior to a scattered radiation removing effect in an X-ray computed tomographic apparatus. Scattered radiation correction is indispensable for extracting low-contrast information as of soft tissue by using three-dimensional imaging using a two-dimensional detector.

Scattered radiation is approximately modeled from primary X-rays passing through a subject to be examined. In practice, however, it is only possible to actually measure a composite image P'(x, y) comprising primary X-rays P(x, y) and scattered radiation S(x, y) like that represented by equation (1):

$$P'(x,y)=P(x,y)+S(x,y) \quad <1>$$

In addition, the scattered radiation S(x, y) can be modeled like equation (2):

$$S(x,y)=\{-P(x,y)\log P(x,y)\}*[A\exp\{-(x^2+y^2)/(2a^2)\}+B\exp\{-(x^2+y^2)/(2b^2)\}] \quad <2>$$

where the symbol "*" represents a convolution operator. The term with the coefficient A is obtained by modeling Rayleigh scattering, and the term with the coefficient B is obtained by modeling Compton scattering. Scattered radiation correction is used to derive the primary X-rays P(x, y) from the composite image P'(x, y) according to equations (1) and (2).

It is, however, impossible to analytically calculate equations (1) and (2), and hence is impossible to directly obtain P(x, y). A conventional technique, therefore, calculates $P_g(x, y)$ which minimizes equation (3) by a successive approximation method.

$$E=|P'(x,y)-P_g'(x,y)|^2 \quad <3>$$

where $P_g'(x, y)$ is a composite image calculated based on $P_g(x, y)$, which can be represented by $$P_g'(x,y)=P_g(x,y)+S_g(x,y) \quad <4>$$

In this case, $S_g(x, y)$ is written as follows:

$$S_g(x,y)=\{-P_g(x,y)\log P_g(x,y)\}*[A\exp\{-(x^2+y^2)/(2a^2)\}+B\exp\{-(x^2+y^2)/(2b^2)\}] \quad <5>$$

Conventional scattered radiation correction, however, requires successive approximation calculation using equation (3) given above for each projection direction. For this reason, calculation processing requires much time.

BRIEF SUMMARY OF THE INVENTION

The present invention has been made in consideration of the above situation, and has as its object to provide a scattered radiation correction method and a scattered radiation correction apparatus which can execute scattered radiation correction at high speed as compared with the prior art in CT-like imaging.

According to an aspect of the present invention, there is provided a scattered radiation correction method which removes scattered radiation from a plurality of projection images collected by CT-like imaging, which comprises, when estimating to identify a scattered radiation image from a projection image in an arbitrary projection direction, setting a scattered radiation image in an adjacent projection direction which is already identified, as an initial estimation image of the scattered radiation images.

According to another aspect of the present invention, there is provided a scattered radiation correction method which removes scattered radiation from a plurality of projection images collected by CT-like imaging, which comprises estimating common scattered radiation images in projection directions from θi to θj.

According to yet another aspect of the present invention, there is provided a scattered radiation correction method which comprises generating a reduced image for an X-ray collection image; identifying a first scattered radiation image on the basis of the reduced image; generating a second scattered radiation image by enlarging the first scatted radiation image; and subtracting the second scattered radiation image from the x-ray collection image, thereby correcting the scattered radiation.

According to yet another aspect of the present invention, there is provided a scattered radiation correction method which removes scattered radiations from a plurality of projection images collected by CT-like imaging, and which comprises generating a reduced image which is common to adjacent i-th and j-th projection direction; identifying a first scattered radiation image on the basis of the reduced image; generating a second scattered radiation image by enlarging the first scatted radiation image; and subtracting the second scattered radiation image from each of the respective collection images, thereby correcting the scattered radiation.

According to yet another aspect of the present invention, there is provided a scattered radiation correction method which removes scattered radiations from a plurality of projection images collected by CT-like imaging, and which comprises, in order to identify a scattered radiation image based on a reduced image from among projection images obtained in an arbitrary projection direction, setting a scattered radiation image in an adjacent projection direction which is already identified, as an initial estimation image of the scattered radiation images.

According to yet another aspect of the present invention, there is provided a scattered radiation correction apparatus which removes scattered radiation from a plurality of projection images collected by CT-like imaging, which comprises an estimation unit which sets a scattered radiation image in an adjacent projection direction which is already identified, as an initial estimation image of the scattered radiation images when a scattered radiation image from a projection image in an arbitrary projection direction is identified.

According to yet another aspect of the present invention, there is provided a scattered radiation correction apparatus which removes scattered radiation from a plurality of projection images collected by CT-like imaging, which comprises an estimation unit which estimates common scattered radiation images in projection directions from θi to θj.

According to yet another aspect of the present invention, there is provided a scattered radiation correction apparatus which comprises a generating unit which generates a reduced image for an X-ray collection image; an identifying unit which identifies a first scattered radiation image on the basis of the reduced image; a generating unit which generates a second scattered radiation image by enlarging the first scattered radiation image; and a subtracting unit which subtract the second scattered radiation image from the x-ray collection image, thereby correcting the scattered radiation.

According to yet another aspect of the present invention, there is provided a scattered radiation correction apparatus which removes scattered radiations from a plurality of projection images collected by CT-like imaging, and which comprises a generating unit which generates a reduced image which is common to adjacent i-th and j-th projection direction; an identifying unit which identifies a first scattered radiation image on the basis of the reduced image; a generating unit which generates a second scattered radiation image by enlarging the first scatted radiation image; and a subtracting unit which subtract the second scattered radiation image from each of the respective collection images, thereby correcting the scattered radiation.

According to yet another aspect of the present invention, there is provided a scattered radiation correction apparatus which removes scattered radiations from a plurality of projection images collected by CT-like imaging, and which comprises: a first unit which sets a reduced scattered radiation image in an adjacent projection direction which is already identified, as an initial estimation image of the reduced scattered radiation images in the adjacent projection direction; and a second unit which identifies a scattered radiation image from among the projection images obtained in an arbitrary projection direction by using the initial estimation image.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

Figure 1:
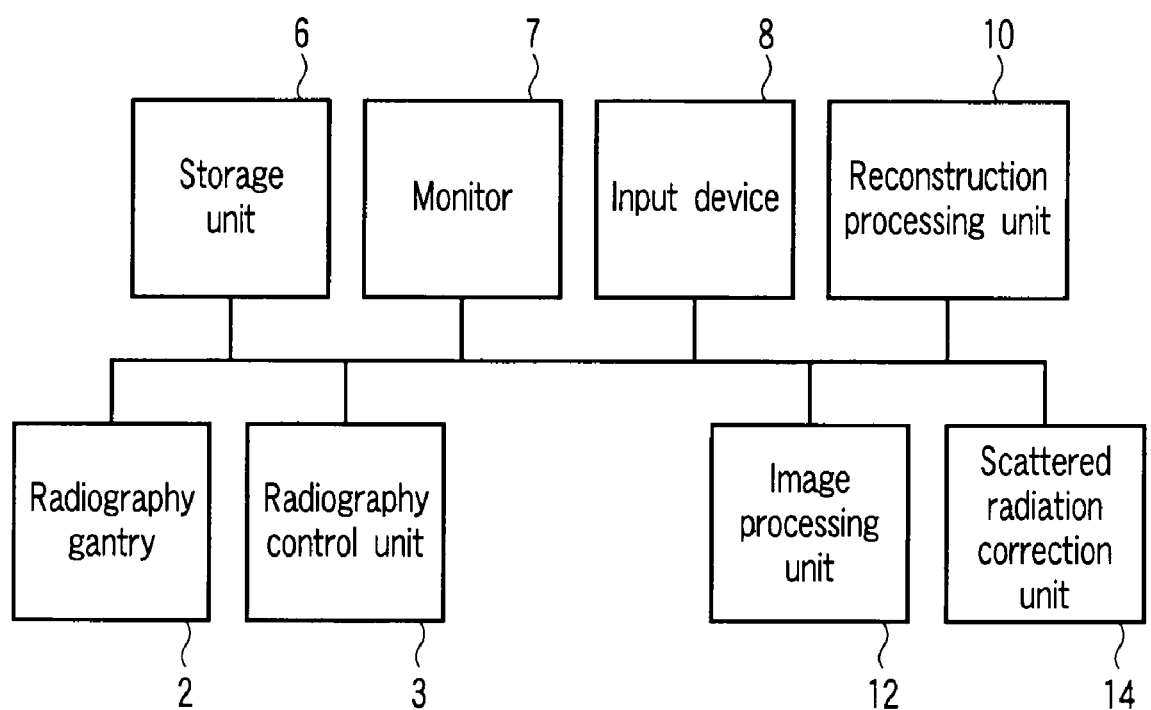
FIG. 1 is a block diagram showing the arrangement of an X-ray diagnostic apparatus 1 according to an embodiment.

An embodiment of the present invention will be described below with reference to the views of the accompanying drawing. Note that in the following description, the same reference numerals denote constituent elements having almost the same functions and arrangements, and a repetitive description will be made only when required.

FIG. 1 shows the arrangement of an X-ray diagnostic apparatus 1 according to this embodiment. The X-ray diagnostic apparatus 1 comprises a radiography gantry 2, radiography control unit 3, storage unit 6, monitor 7, input device 8, reconstruction processing unit 10, image processing unit 12, and scattered radiation correction unit 14.

Figure 2:
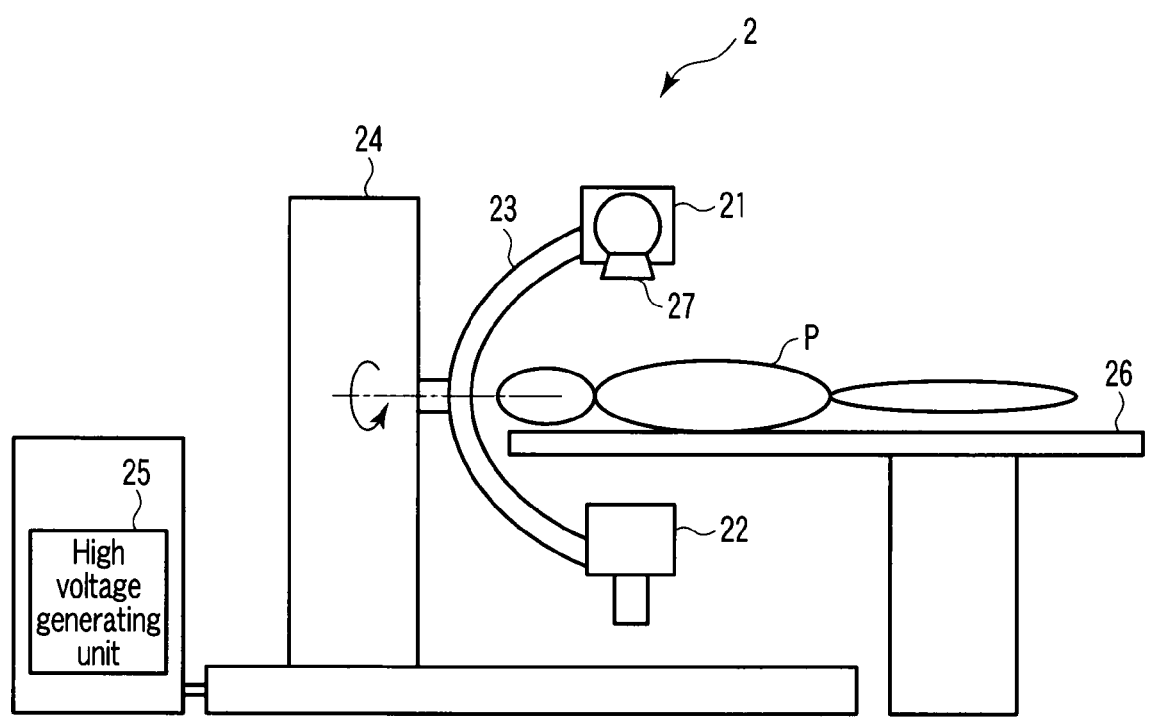
FIG. 2 is a view showing an example of the outer appearance of a radiography gantry 2.

FIG. 2 shows an example of the outer appearance of the radiography gantry 2. As shown in FIG. 2, the radiography gantry 2 includes an X-ray tube 21, X-ray detector 22, C-arm 23, stand 24, high voltage generating unit 25, bed 26, and X-ray stop device 27.

The high voltage generating unit 25 generates a high voltage to be applied between the electrodes of the X-ray tube 21, and also generates a filament current to be supplied to the cathode filament of the X-ray tube 21. Upon receiving the high voltage and filament current, the X-ray tube 21 generates X-rays. The X-ray stop device 27 shapes X-rays generated by the X-ray tube 21. The X-ray detector 22 is typically a solid flat panel detector comprising a two-dimensional array of a plurality of detection elements (pixels) which directly or indirectly convert incident X-rays into electric charges. The X-ray tube 21 is mounted on, for example, one end of the floor type C-arm 23. The X-ray detector 22 is mounted on the other end of the C-arm 23. The X-ray detector 22 faces the X-ray tube 21 through a subject P to be examined which is placed on the bed 26. The C-arm 23 is rotatably supported on the stand 24. Repeating radiography with respect to the subject P while rotating the C-arm 23 makes it possible to acquire X-ray images (projection images) in many directions which are required for three dimensional image reconstruction.

The radiography control unit 3 controls the rotation of the C-arm 23, the application of high voltages from the high voltage generating unit 25 to the X-ray tube 21, and reading of signals from the X-ray detector 22 in order to execute rotational radiography and generate X-ray image data.

The storage unit 6 stores a dedicated program for executing a scattered radiation correction function to be described later.

The monitor 7 is a display device such as a CRT, plasma display, or liquid crystal display which displays an X-ray diagnostic image or the like in a predetermined form in accordance with a signal received from the reconstruction processing unit 10 or the image processing unit 12.

The input device 8 includes a keyboard, various kinds of switches, a mouse, and the like and is used to input a radiography instruction, image selection instruction, and the like.

The reconstruction processing unit 10 reconstructs volume data from projection images in a plurality of projection directions.

The image processing unit 12 executes predetermined image processing such as volume rendering processing and image difference processing as needed.

The scattered radiation correction unit 14 implements the scattered radiation correction function (to be described later) by, for example, loading the dedicated program from the storage unit 6 into the memory.

(Scattered Radiation Correction Function)

The scattered radiation correction function of the X-ray diagnostic apparatus 1 will be described next. This function is used to perform correction (scattered radiation correction) to acquire primary X-ray image data by generating a reduced image of each projection image acquired by CT-like imaging, estimating a first scattered radiation image of each projection image by using each reduced image, obtaining a second scattered radiation image by enlarging the first scattered radiation image, and removing the second scattered radiation image from each projection image.

Note that this embodiment will exemplify a case wherein a scattered radiation estimation processing according to the present invention is applied to an X-ray diagnostic apparatus 1. However, the present invention is not limited to X-ray diagnostic apparatus and can be applied to any techniques which perform the scattered radiation estimation processing such as a scattered radiation estimation processor, which is different to an X-ray diagnostic apparatus and for example, a workstation installed a dedicated program for executing a scattered radiation correction function.

Figure 3:
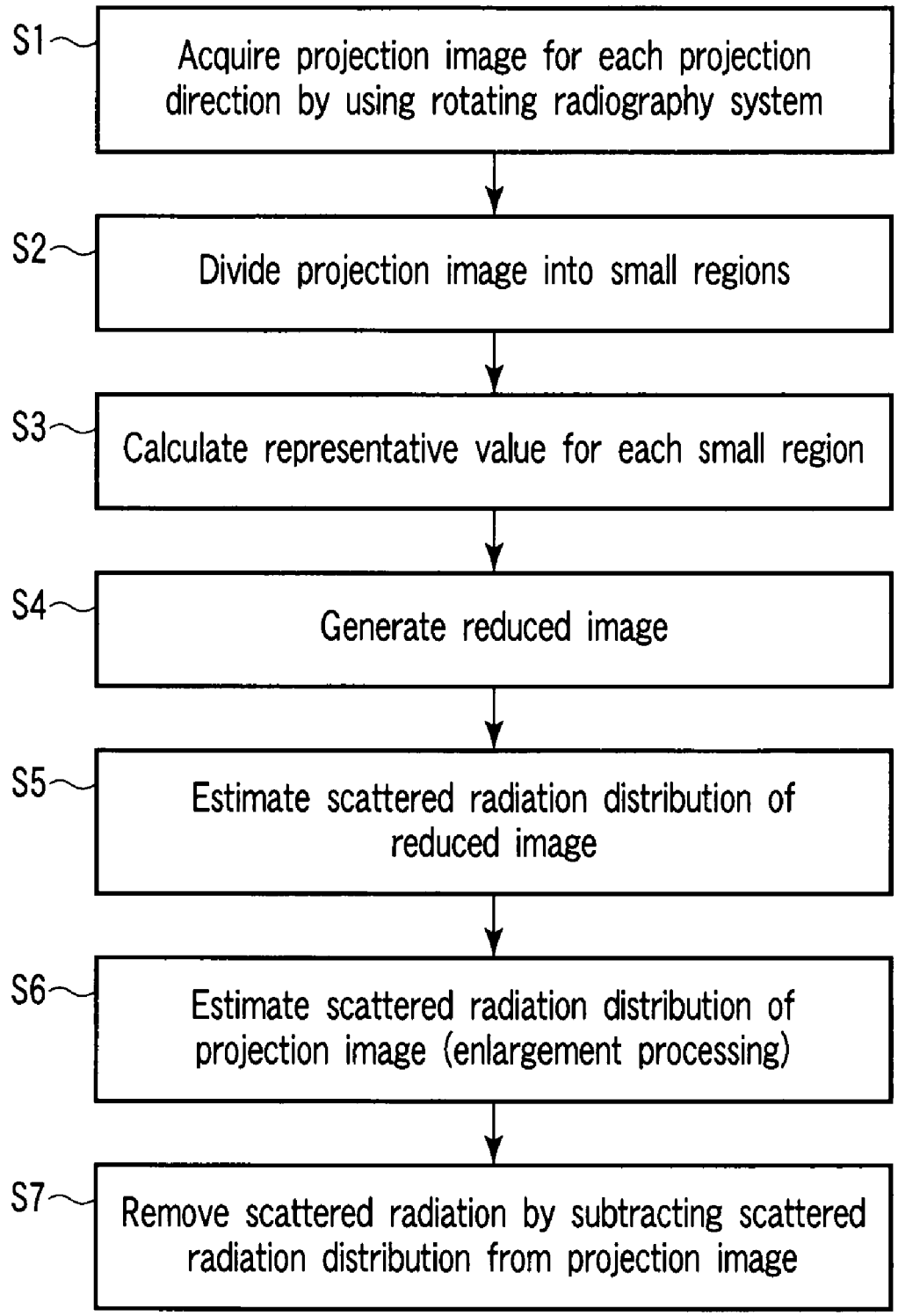
FIG. 3 is a flowchart showing a procedure for processing (scattered radiation estimation processing) based on a scattered radiation estimation function according to the first embodiment.

FIG. 3 is a flowchart showing a procedure for processing (scattered radiation estimation processing) based on this scattered radiation estimation function. As shown in FIG. 3, first of all, the C-arm 23 continuously rotates about the body axis as a rotation axis under the control of the radiography control unit 4, and a plurality of projection images in different radiographing directions are acquired by repeatedly executing radiography for the subject P during this rotation (step S1). For example, the C-arm 23 rotates for four sec at a rate of 50°/sec, and about 200 frames of X-ray images are acquired during this period. The storage unit 6 stores the acquired projection images in association with data indicating the respective projection directions.

Figure 4:
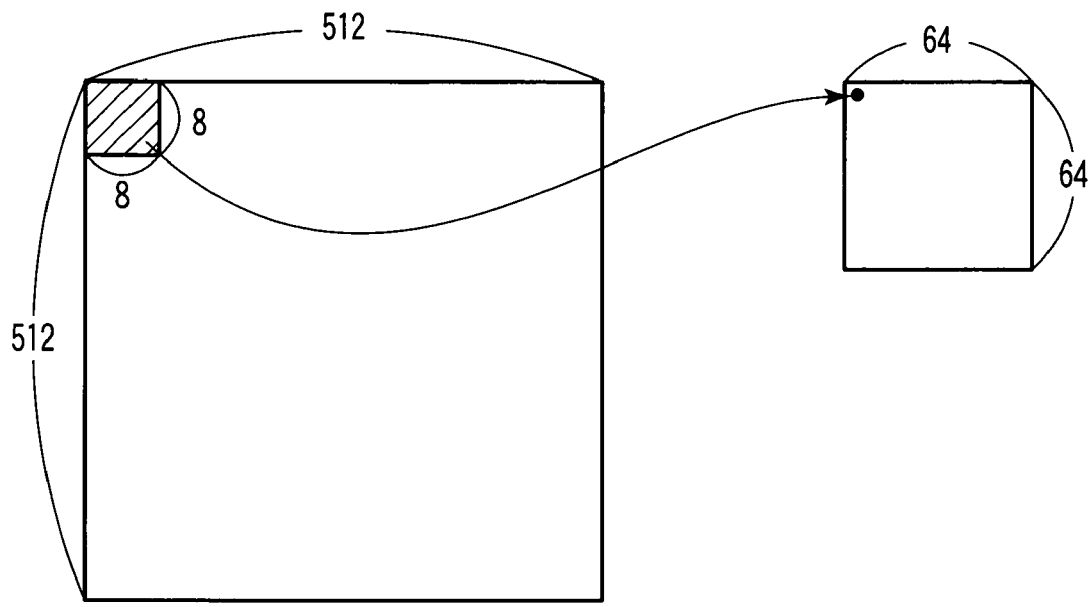
FIG. 4 is a view for explaining processing in step S4 in FIG. 3.

The scattered radiation correction unit 14 then divides a projection image in a predetermined projection direction into a plurality of small regions (step S2). The size and number of such small regions are not specifically limited. For example, if the size of a projection image is 512 pixels×512 pixels as shown in FIG. 4, the size of each small region is set to 8 pixels×8 pixels, and the projection image is divided into a total of 64 small regions.

The scattered radiation correction unit 14 calculates the representative value of each small region (step S3). In this case, a representative value is, for example, the average value, maximum value, or median of the pixels contained in a small region. Assume that this embodiment uses the average value of the pixels contained in each small region as a representative value in consideration of the scattered radiation of all the pixels in each small region.

The scattered radiation correction unit 14 then maps the respective representative values such that they correspond to the positions of the respective small regions on a projection image, thereby generating a reduced image associated with the projection image (step S4). In the case shown in FIG. 4, a reduced image of 64 pixels×64 pixels is generated from a projection image of 512 pixels×512 pixels.

Figure 5:
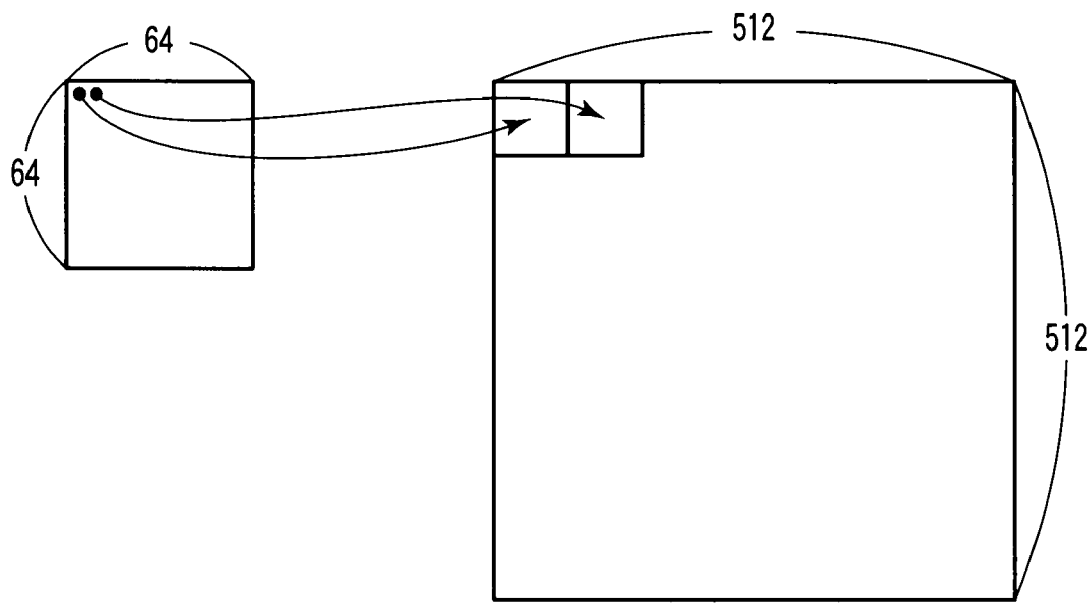
FIG. 5 is a view for explaining processing in step S6 in FIG. 3.

The scattered radiation correction unit 14 estimates a scattered radiation distribution of the reduced small image on the basis of a predetermined technique or the like implemented by the calculation program stored in the storage unit 6 (step S5). The scattered radiation correction unit 14 identifies a scattered radiation distribution of the projection image by enlarging the scattered radiation distribution of the estimated reduced image (step S6). That is, as shown in FIG. 5, the scattered radiation correction unit 14 performs mapping to make the respective pixel values of the reduced image correspond to pixel values at predetermined positions in the small regions (e.g., the central positions or nearby positions) on the projection image. Thereafter, the scattered radiation correction unit 14 estimates a scattered radiation distribution of the projection image by calculating pixels values at other positions in the respective small regions by, for example, interpolation processing.

Subsequently, the scattered radiation correction unit 14 executes scattered radiation correction of the projection image by subtracting the obtained scattered radiation distribution from the projection image (step S7). Note that the processing in steps S2 to S7 is executed for a projection image in each projection direction.

As described above, this X-ray diagnostic apparatus estimates scattered radiation by using a reduced image generated from a projection image, and estimates a scattered radiation distribution of the projection image by enlarging the estimated scattered radiation. This makes it possible to reduce the amount of data to be processed in estimation of a scattered radiation distribution and execute scattered radiation correction at high speed as compared with the conventional technique of estimating a scattered radiation distribution by using the projection image obtained by radiography itself.

Since a scattered radiation image is composed mainly of low-frequency components, the estimation based on a reduced image does not lower the accuracy.

It should be noted that the embodiments describe the cases where the technical concept of the present invention is applied to the CT-like imaging. However, the present invention is not limited to these embodiments, but the invention is also usefully applicable to the correction of scattered radiation in an X-ray image shot from one direction.

Second Embodiment

A scattered radiation correction function according to the second embodiment of the present invention will be described next. The distributions of projection images in adjacent projection directions acquired by CT-like imaging tend to be approximate to each other. This is because low-frequency components are dominant in the radiation distribution included in a projection image. In addition, since low frequency components are generally dominant in the distribution of a scattered radiation image, the CT value distributions of scattered radiation contained in projection images in adjacent projection directions are further approximate to each other. The scattered radiation correction function according to this embodiment speeds up scattered radiation estimation in a projection direction adjacent to a predetermined projection direction by using a scattered radiation image which has already been identified in the predetermined projection direction.

Figure 6:
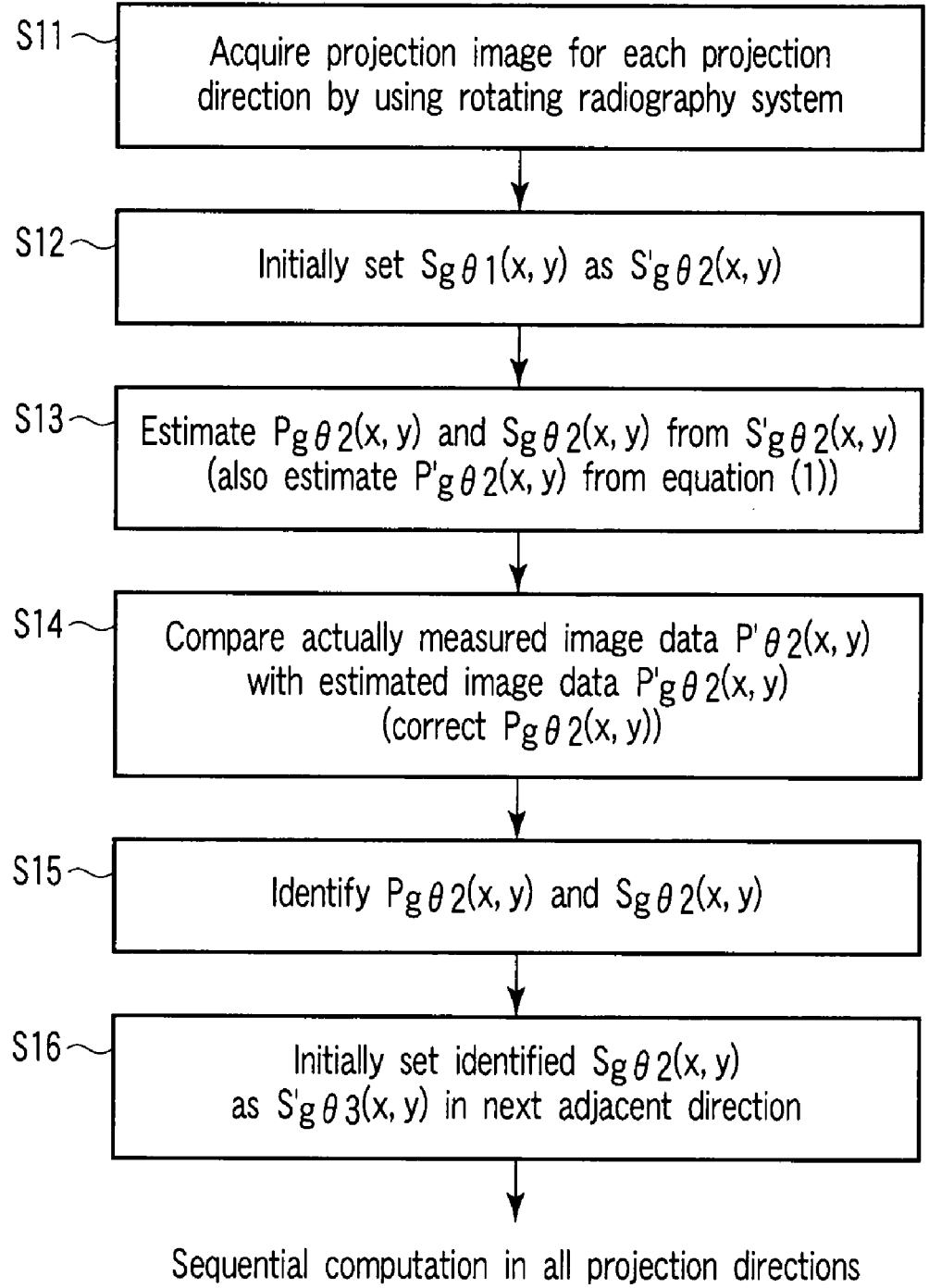
FIG. 6 is a flowchart showing a scattered radiation estimation processing procedure according to the second embodiment.

FIG. 6 is a flowchart showing a scattered radiation estimation processing procedure according to this embodiment. As shown in FIG. 6, first of all, a C-arm 23 continuously rotates about the body axis as a rotation axis under the control of a radiography control unit 3, and a plurality of projection images in different radiographing directions are acquired by repeatedly executing radiography for a subject P to be examined during this rotation (step S11). A storage unit 6 stores the acquired projection images in association with data indicating the projection directions.

A scattered radiation correction unit 14 then initially sets scattered radiation data $S_{g\theta1}(x, y)$ as scattered radiation data $S_{g\theta2}(x, y)$ which is initial value of scattered radiation data $S_{g\theta2}(x, y)$ in a predetermined projection direction θ2 adjacent to projection direction θ1 (step S12). A technique for this initial setting is not specifically limited.

The scattered radiation correction unit 14 then calculates primary X-ray data $P_{g\theta2}(x, y)$ on the basis of the initially set scattered radiation data $S'_{\theta2}(x, y)$ and the acquired projection data $P'_{g\theta2}(x, y)$, and calculates scattered radiation data $S_{g\theta2}(x, y)$ corresponding to primary X-ray data $P_{g\theta2}(x, y)$ by using equation (2). In addition, the scattered radiation correction unit 14 estimates projection image data by using equation (A) given below (step S13):

$$P'_{g\theta2}(x,y) = P_{g\theta2}(x,y) + S_{g\theta2}(x,y) \qquad \langle A \rangle$$

Note that the projection image data estimated by using equation (A) will be referred to as estimated image data $P'_{gn2}(x, y)$.

The scattered radiation correction unit 14 compares the estimated image data $P'_{g\theta2}(x, y)$ with the projection image data (to be referred to as actually measured image data $P'_{\theta2}(x, y)$) actually acquired in step S11, and corrects the primary X-ray data $P_{g\theta2}(x, y)$ (step S14). In addition, the scattered radiation correction unit 14 repeats the processing in steps S13 and S14 a plurality of number of times by using the corrected primary X-ray data $P_{g\theta2}(x, y)$ as needed. If, for example, the similarity (e.g., the correlation value) between the estimated image data $P'_{g\theta2}(x, y)$ and the actually measured image data $P'_{\theta2}(x, y)$ becomes equal to or more than a threshold as a result of the repetitive execution of the processing, the data $P_{g\theta2}(x, y)$ is identified as a primary X-ray image in the predetermined projection direction, and the data $S_{g\theta2}(x, y)$ is identified as scattered radiation data in the predetermined projection direction (step S15).

The scattered radiation correction unit 14 sets the identified scattered radiation data $S_{g\theta2}(x, y)$ as initial X-ray data $S'_{g\theta3}(x, y)$ of scattered radiation data $S_{g\theta3}(x, y)$ in a next projection direction $\theta3$ adjacent to the predetermined projection direction $\theta2$ (step S16), and executes the processing from step S12 to step S15 described above to identify the primary X-ray data $P_{g\theta3}(x, y)$ and the scattered radiation data $S_{g\theta3}(x, y)$ in the projection direction $\theta3$. Subsequently, similar calculation is sequentially executed in each projection direction up to en to identify primary X-ray data $P_{g\theta n}(x, y)$ and scattered radiation data $S_{g\theta n}(x, y)$ in each projection direction.

As described above, when obtaining a primary X-ray image and a scattered radiation distribution in each projection direction, this X-ray diagnostic apparatus uses a primary X-ray image in an adjacent direction which has already been identified as the initially estimated value (initially set value) in the next sequential calculation. Since an initially set value of a scattered radiation image in each projection direction is very close to a scattered radiation image which is to be identified, it is possible to estimate scattered radiation distributions and primary X-ray images at high speed.

Third Embodiment

A scattered radiation correction function according to the third embodiment of the present invention will be described next. The scattered radiation correction function according to this embodiment is to approximate scattered radiation images (distributions) in n adjacent projection directions to each other when the angle intervals (i.e., the intervals of the angles in which projection is carried out) is small so as to speed up scattered radiation correction.

Figure 7:
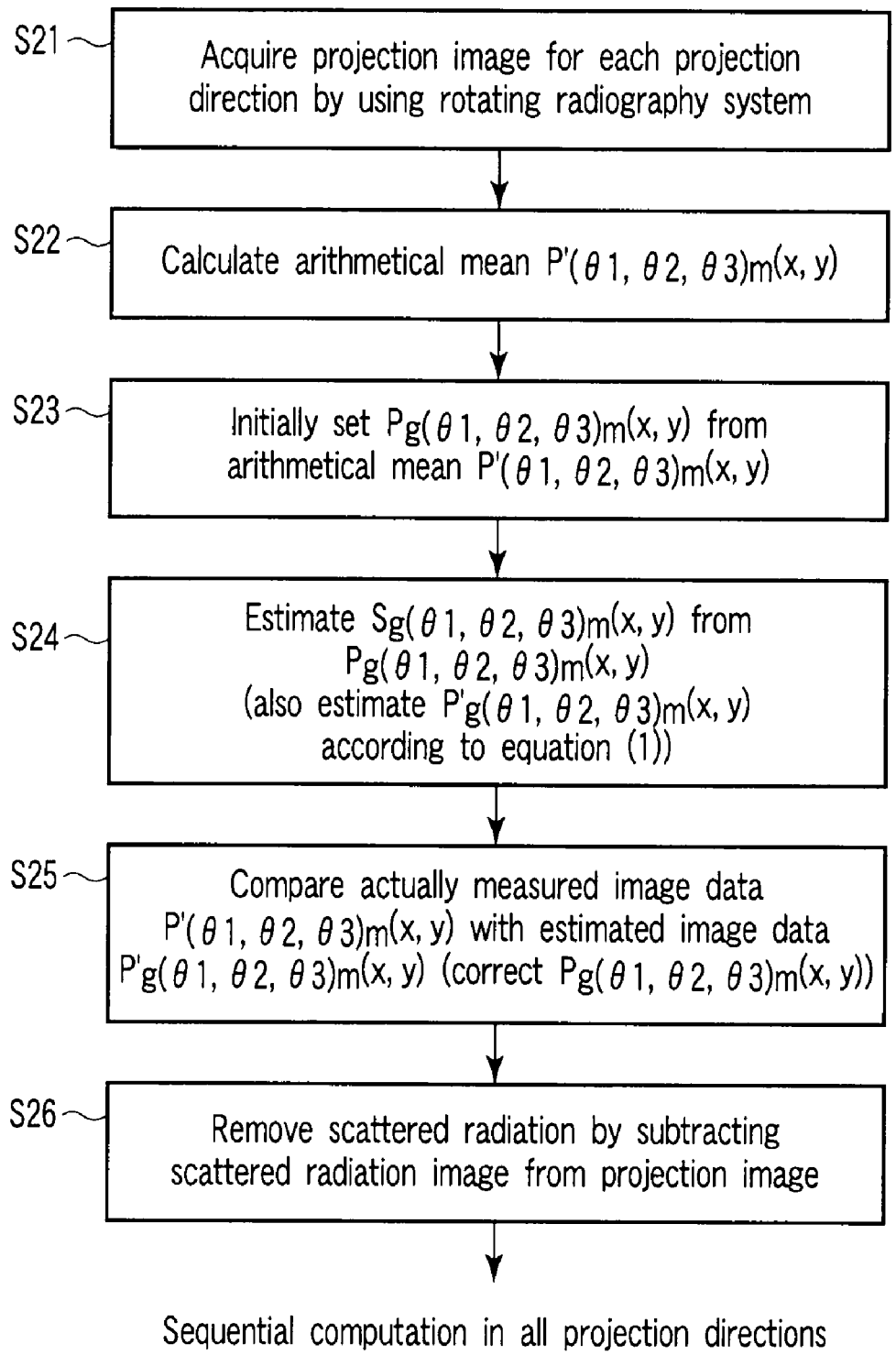
FIG. 7 is a flowchart showing a scattered radiation estimation processing procedure according to the third embodiment.

FIG. 7 is a flowchart showing a scattered radiation estimation processing procedure according to this embodiment. As shown in FIG. 7, first of all, a C-arm 23 continuously rotates about the body axis as a rotation axis under the control of a radiography control unit 3, and a plurality of projection images in different radiographing directions are acquired by repeatedly executing radiography for a subject P to be examined during this rotation (step S21). A storage unit 6 stores the acquired projection images in association with data indicating the projection directions.

A scattered radiation correction unit 14 then calculates arithmetical mean image data $P'_{(\theta1, \theta2, \theta3)m}(x, y)$ of projection image data $P'_{\theta1}(x, y)$, $P'_{\theta2}(x, y)$, and $P'_{\theta3}(x, y)$ in n (three in this case) adjacent projection directions $\theta1$, $\theta2$, and $\theta3$ (step S22). The scattered radiation correction unit 14 also initially sets primary X-ray image data $P'_{(\theta1, \theta2, \theta3)m}(x, y)$ in the projection directions $\theta1$, $\theta2$, and $\theta3$ by using the arithmetical mean image data $P_{g(\theta1, \theta2, \theta3)m}(x, y)$ (step S23).

The scattered radiation correction unit 14 then estimates scattered radiation data $S_{g(\theta1, \theta2, \theta3)m}(x, y)$ on the basis of the initially set primary X-ray data $P_{g(\theta1, \theta2, \theta3)m}(x, y)$ and acquires estimated image data $P'_{g(\theta1, \theta2, \theta3)m}(x, y)$ by using equation (1) given above (step S24).

The scattered radiation correction unit 14 compares the estimated image data $P'_{g(\theta1, \theta2, \theta3)m}(x, y)$ with the arithmetical mean image data $P'_{(\theta1, \theta2, \theta3)m}(x, y)$ calculated in step S22 and corrects the initially set primary X-ray data $P_{g(\theta1, \theta2, \theta3)m}(x, y)$ (step S25). The scattered radiation correction unit 14 also repeats the processing in steps S24 and S25 a plurality of number of times by using the corrected primary X-ray data $P_{g(\theta1, \theta2, \theta3)m}(x, y)$ as needed. If the similarity between the estimated image data $P'_{g(\theta1, \theta2, \theta3)m}(x, y)$ and the arithmetical mean image data $P'_{(\theta1, \theta2, \theta3)m}(x, y)$ becomes equal to or more than a threshold as a result of the repetitive execution of the processing, the data $S_{g(\theta1, \theta2, \theta3)m}(x, y)$ is identified as scattered radiation data in the projection directions $\theta1$, $\theta2$, and $\theta3$ and the primary X-ray data $P_{\theta1}(x, y)$, $P_{\theta2}(x, y)$, and $P_{\theta3}(x, y)$ is identified by subtracting the data $S_{g(\theta1, \theta2, \theta3)m}(x, y)$ from projection image data $P'_{\theta1}(x, y)$, $P'_{\theta2}(x, y)$, and $P'_{\theta3}(x, y)$ respectively (step S26).

Subsequently, similar calculation is sequentially executed in the projection directions up to $\theta n$ for every three adjacent projection directions to identify primary X-ray data and scattered radiation data in each projection direction.

As described above, when obtaining a primary X-ray image and a scattered radiation distribution in each projection direction by sequential approximation calculation, the X-ray diagnostic apparatus according to this embodiment uses common initially set values in n adjacent projection directions assuming that scattered radiation distributions in the n adjacent projection directions are approximate to each other. Therefore, there is no need to perform calculation for estimation of the scattered radiation image in each projection direction, unlike the prior art, and hence it is possible to estimate scattered radiation distributions and primary X-ray images at high speed.

Fourth Embodiment

A scattered radiation correction function according to the fourth embodiment of the present invention will be described next. Then scattered radiation correction function according to this embodiment is a combination of the first and second embodiments.

Figure 8A:
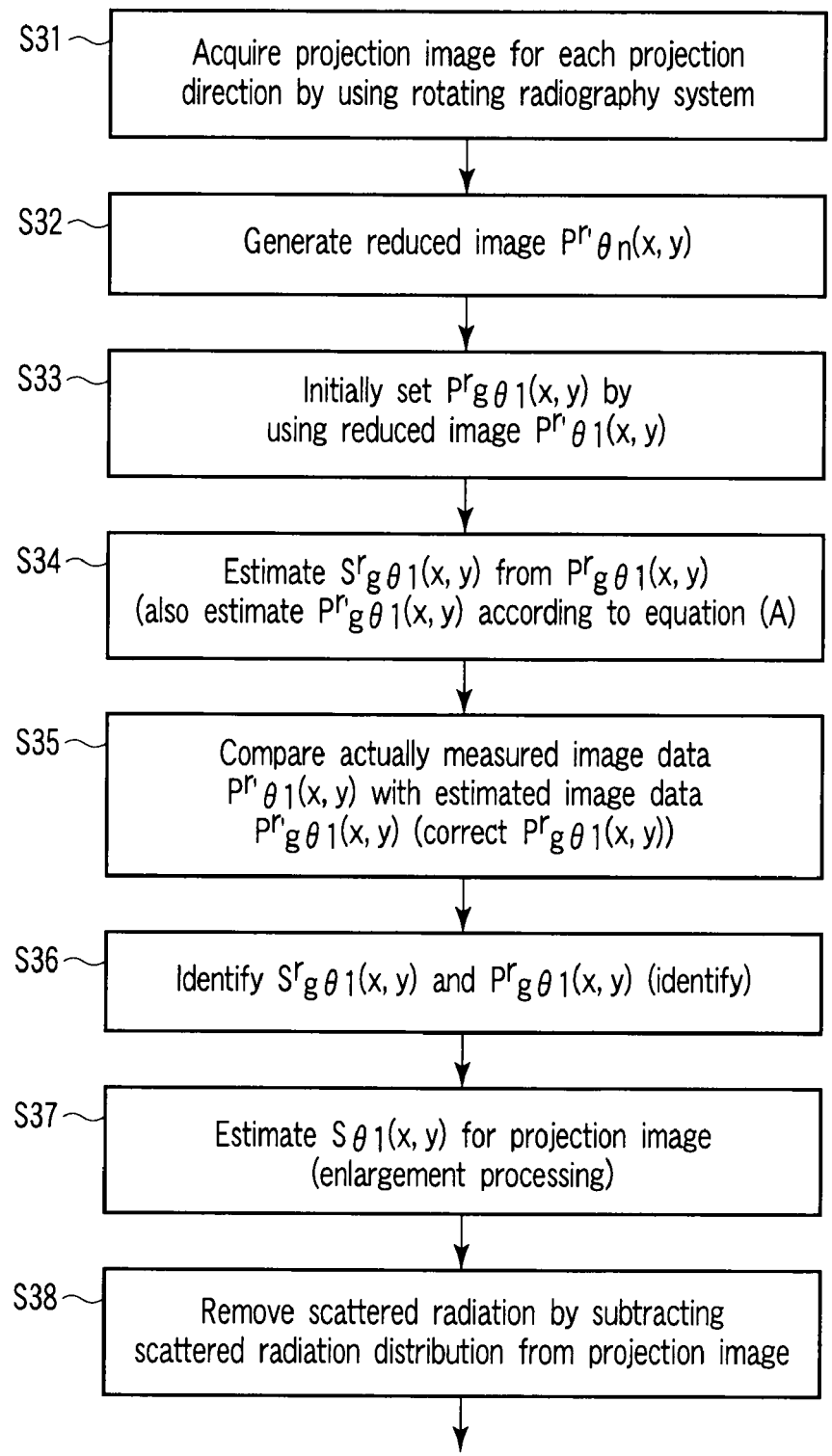
FIGS. 8A and 8B are flowcharts showing a scattered radiation estimation processing procedure according to the fourth embodiment.
Figure 8B:
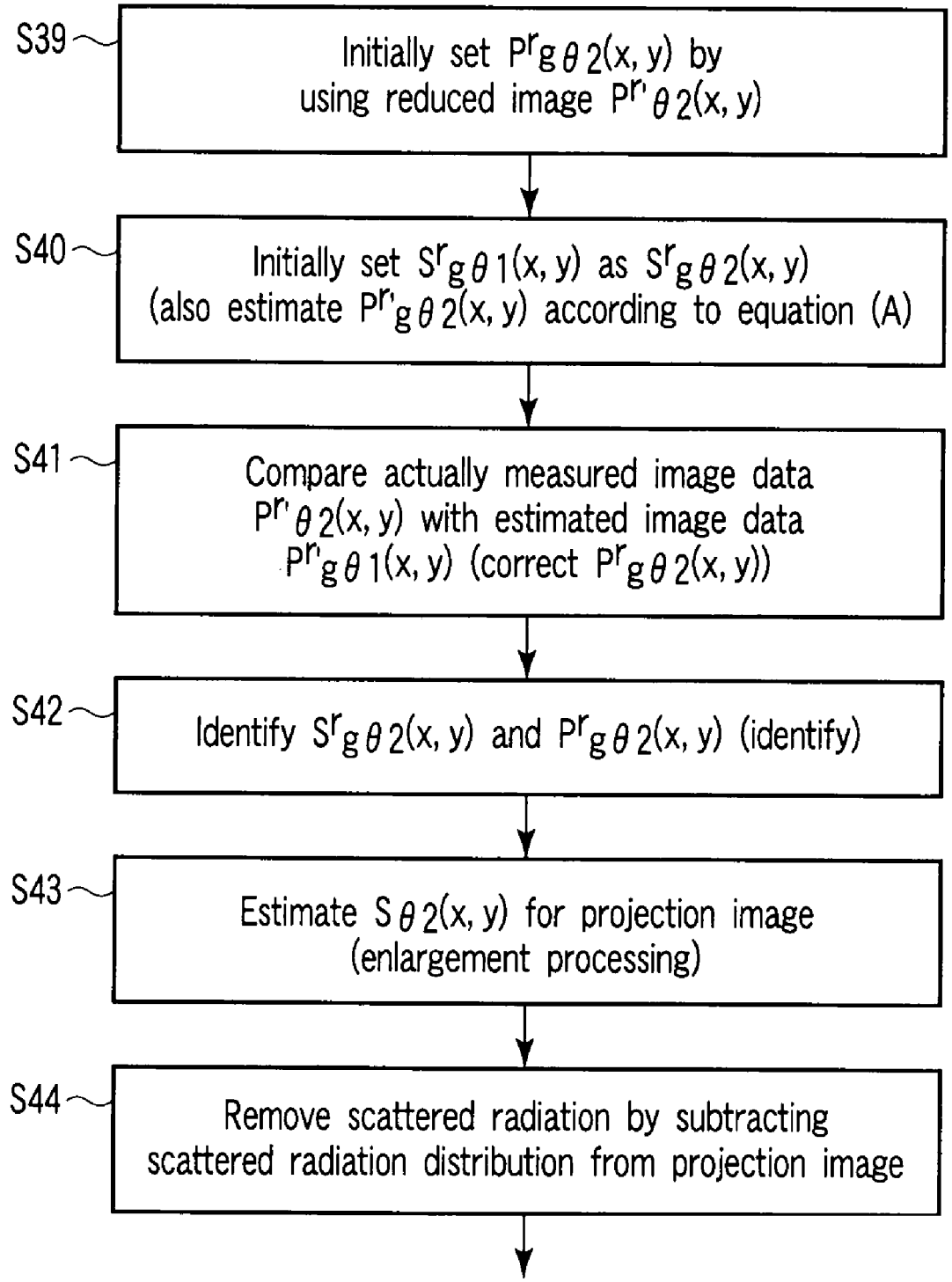

FIGS. 8A and 8B are flowcharts showing a scattered radiation estimation processing procedure according to this embodiment. As shown in FIG. 8, first of all, a C-arm 23 continuously rotates about the body axis as a rotation axis under the control of a radiography control unit 3, and a plurality of projection images in different radiographing directions are acquired by repeatedly executing radiography for a subject P to be examined during this rotation (step S31). A storage unit 6 stores the acquired projection images in association with data indicating the projection directions.

A scattered radiation correction unit 14 generates a reduced image $P''_{\theta n}(x, y)$ of the projection image in each projection direction $\theta n$ (step S32). A technique for generating reduced images is the same as that described above.

The scattered radiation correction unit 14 initially sets primary X-ray data $P^r_{\theta 1}(x, y)$ in a projection direction $\theta 1$ by using the reduced image $P''_{\theta 1}(x, y)$ (step S33). The scattered radiation correction unit 14 estimates scattered radiation data $S^r_{g\theta 1}(x, y)$ on the basis of the initially set primary X-ray data $P^r_{g\theta 1}(x, y)$, and acquires estimated image data $P''^r_{g\theta 1}(x, y)$ by using equation (1) (step S34).

The scattered radiation correction unit 14 compares the estimated image data $P''_{g\theta 1}(x, y)$ with the reduced image data $P''_{\theta 1}(x, y)$ generated in step S32, and corrects the primary X-ray data $P^r_{g\theta 1}(x, y)$ initially set in step S33 (step S35). The scattered radiation correction unit 14 also repeats the processing in steps S34 and S35 a plurality of number of times by using the corrected primary X-ray data $P^r_{g\theta 1}(x, y)$ as needed. If, for example, the similarity (e.g., the correlation value) between the estimated image data $P''_{g\theta 1}(x, y)$ and the actually measured image data $P''_{\theta 1}(x, y)$ becomes equal to or more than a threshold as a result of the repetitive execution of the processing, the data $P^r_{g\theta 1}(x, y)$ is identified as primary X-ray image in the predetermined projection direction, and the data $S^r_{g\theta 1}(x, y)$ is identified as scattered radiation data in the predetermined projection direction (step S36).

The scattered radiation correction unit 14 enlarges the scattered radiation distribution of the estimated reduced image, and identifies a scattered radiation distribution $S_{g\theta 1}(x, y)$ of the projection image (step S37). The scattered radiation correction unit 14 executes scattered radiation correction of the projection image by subtracting the obtained scattered radiation distribution from the projection image (step S38).

Next, the scattered radiation correction unit 14 initially sets primary X-ray data $P^r_{g\theta 2}(x, y)$ relating to projection direction $\theta 2$ by using the reduced image data $P''_{\theta 2}(x, y)$. In addition, the scattered radiation correction unit 14 initially sets already-identified scattered radiation data $S^r_{g\theta 1}(x, y)$ as scattered radiation data $S^r_{g\theta 2}(x, y)$ relating to projection direction $\theta 2$ (step S39). By use of the initially-set primary X-ray data $P^r_{g\theta 2}(x, y)$ and scattered radiation data $S^r_{g\theta 1}(x, y)$, the scattered radiation correction unit 14 acquires estimated image data $P''_{g\theta 2}(x, y)$ based on formula (A) (step S40).

The scattered radiation correction unit 14 compares the estimated image data $P''_{g\theta 2}(x, y)$ with the reduced image data $P''_{\theta 1}(x, y)$ generated in step S32, and corrects the primary X-ray data $P^r_{g\theta 2}(x, y)$ initially set in step S39 (step S41). When necessary, the scattered radiation correction unit 14 repeats the processing of steps S39 and S40 a number of times by use of the corrected primary X-ray data $P^r_{g\theta 2}(x, y)$. If, after the repeated processing, the similarity (e.g., a correlation value) between the estimated image data $P''_{g\theta 2}(x, y)$ and actually-measured image data $P''_{\theta 2}(x, y)$ becomes equal to or more than a predetermined threshold, then image data $P^r_{g\theta 2}(x, y)$ is used as a primary X-ray image relating to the predetermined projection direction, and $S^r_{g\theta 2}(x, y)$ acquired based on formula (A) is identified as the scattered radiation distribution relating to the predetermined projection direction (step S42).

Next, the scattered radiation correction unit 14 enlarges the scattered radiation distribution relating to the identified reduced image, and identifies the scattered radiation distribution $S_{g\theta 2}(x, y)$ relating to the projection image (step S43). In addition, the scattered radiation correction unit 14 executes the scattered radiation correction relating to the projection image by subtracting the obtained scattered radiation distribution from the projection image (step S44). Thereafter, similar calculation is sequentially executed with respect to each of projection directions $\theta 3$ to $\theta n$, so as to execute scattered radiation correction for the projection image obtained in each projection direction. At the time, an already-identified reduced scattered radiation image relating to an adjacent projection direction is used as an initially-set reduced scattered radiation image (for example, when scattered radiation correction is performed with respect to projection direction $\theta n$, the already-identified reduced scattered radiation image with respect to projection direction $\theta n-1$ is used).

As described above, this X-ray diagnostic apparatus identifies a primary X-ray image and a scattered radiation distribution in each projection direction by using a reduced image generated from each projection image and a reduced scattered radiation image in each adjacent direction which has already been identified. Therefore, there is no need to estimate a scattered radiation distribution by using a projection image obtained by radiography itself, unlike the prior art. In addition, the initial estimated value of scattered radiation image of the present invention is further closer to the actual scattered radiation distribution than the initial estimated value in the conventional techniques, and hence it is possible to estimate scattered radiation distributions and primary X-ray images at higher speed. According to the experiments conducted by the present inventors, it is possible to speed up the processing by about 10 times in terms of actual measurements.

Fifth Embodiment

A scattered radiation correction function according to the fifth embodiment of the present invention will be described next. The scattered radiation correction function according to this embodiment is a combination of the first and third embodiments.

Figure 9:
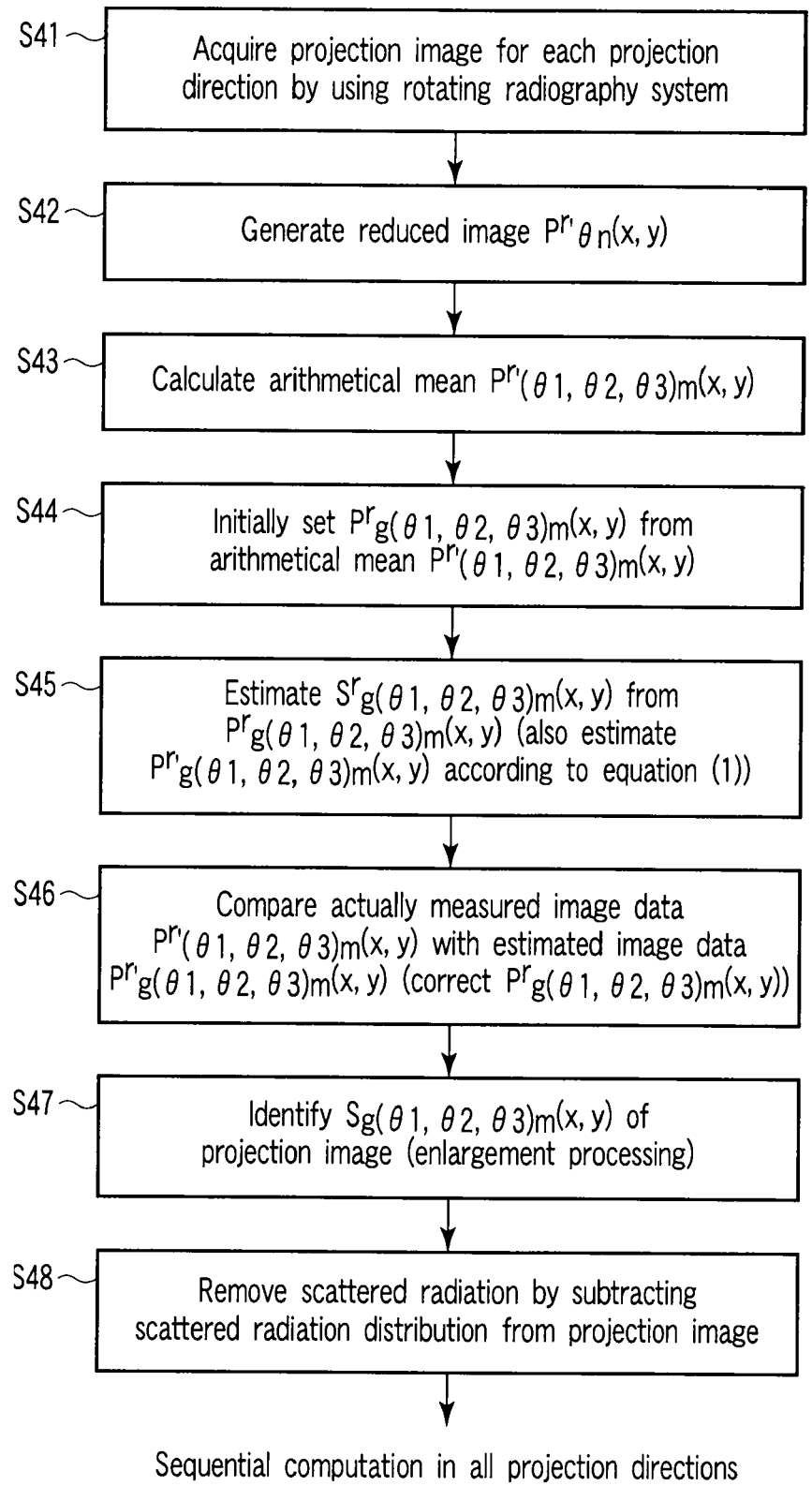
FIG. 9 is a flowchart showing a scattered radiation estimation processing procedure according to the fifth embodiment.

FIG. 9 is a flowchart showing a scattered radiation estimation processing procedure according to this embodiment. As shown in FIG. 9, first of all, a C-arm 23 continuously rotates about the body axis as a rotation axis under the control of a radiography control unit 3, and a plurality of projection images in different radiographing directions are acquired by repeatedly executing radiography for a subject P to be examined during this rotation (step S41). A storage unit 6 stores the acquired projection images in association with data indicating the projection directions.

A scattered radiation correction unit 14 then generates a reduced image for each of projection images in each of projection directions $\theta n$ (step S42). A reduced image generation technique to be used is the same as that described above.

The scattered radiation correction unit 14 then calculates arithmetical mean image data $P''_{(\theta 1, \theta 2, \theta 3)m}(x, y)$ of reduced image data $P''_{\theta 1}(x, y), P''_{\theta 2}(x, y)$, and $P''_{\theta 3}(x, y)$ in n (three in this case) adjacent projection directions $\theta 1, \theta 2$, and $\theta 3$ (step S43). The scattered radiation correction unit 14 also initially sets primary X-ray image data $P^r_{g(\theta 1, \theta 2, \theta 3)m}(x, y)$ in the projection directions $\theta 1, \theta 2$, and $\theta 3$ by using the arithmetical mean image data $P''_{(\theta 1, \theta 2, \theta 3)m}(x, y)$ (step S44).

The scattered radiation correction unit 14 then estimates scattered radiation data $P''_{g(\theta 1, \theta 2, \theta 3)m}(x, y)$ on the basis of the initially set primary X-ray data $S^r_{g(\theta 1, \theta 2, \theta 3)m}(x, y)$ and identifies estimated image data $P''_{g(\theta 1, \theta 2, \theta 3)m}(x, y)$ by using equation (1) given above (step S45).

The scattered radiation correction unit 14 compares the estimated image data $P''_{g(\theta 1, \theta 2, \theta 3)m}(x, y)$ with the arithmetical mean image data $P''_{(\theta 1, \theta 2, \theta 3)m}(x, y)$ calculated in step S22 and corrects the initially set primary X-ray data $P^r_{g(\theta 1, \theta 2,}$ $_{\theta3)m}$(x, y) (step S46). The scattered radiation correction unit 14 also repeats the processing in steps S45 and S46 a plurality of number of times by using the corrected primary X-ray data $P^r{}_{g(\theta1, \theta2, \theta3)m}$(x, y) as needed. If the similarity between the estimated image data $P'^r{}_{g(\theta1, \theta2, \theta3)m}$(x, y) and the arithmetical mean image data $P'^r{}_{(\theta1, \theta2, \theta3)m}$(x, y) becomes equal to or more than a threshold as a result of the repetitive execution of the processing, the scattered radiation correction unit 14 identifies the data $S^r{}_{g(\theta1, \theta2, \theta3)m}$(x, y) as scattered radiation distributions in the projection directions θ1, θ2, and θ3 (step S47). The scattered radiation correction unit 14 enlarges the scattered radiation distribution of the estimated reduced image, and identifies a scattered radiation distribution $S_{g(\theta1, \theta2, \theta3)m}$(x, y) of the projection image (step S47).

The scattered radiation correction unit 14 executes scattered radiation correction of the projection images in the projection directions θ1, θ2, and θ3 by subtracting the obtained scattered radiation distributions from the projection images (step S48). Subsequently, similar calculation is sequentially executed in each projection direction up to θn for every three adjacent projection directions to identify primary X-ray data and scattered radiation data in each projection direction.

As described above, this X-ray diagnostic apparatus identifies a primary X-ray image in each projection direction by using a reduced image generated from each projection image and initially set values common to n adjacent projection directions. Therefore, unlike the conventional techniques, it is not necessary with the present invention to estimate the scattered radiation distribution for each direction, or to carry out the estimation of a scattered radiation image at the size of the original image, and hence it is possible to estimate scattered radiation distributions and primary X-ray images at higher speed.

Note that the present invention is not limited to the above embodiments, and constituent elements can be variously modified and embodied at the execution stage within the spirit and scope of the invention. Various inventions can be formed by proper combinations of a plurality of constituent elements disclosed in the above embodiments. For example, several constituent elements may be omitted from the all the constituent elements in each embodiment. In addition, constituent elements of the different embodiments may be combined as needed.

What is claimed is:

1. A scattered radiation correction method which removes scattered radiation from a plurality of projection images collected by CT-like imaging, the method comprising:
   when estimating to identify a scattered radiation image from a projection image in an arbitrary projection direction, setting a scattered radiation image in an adjacent projection direction which is already identified, as an initial estimation image of the scattered radiation images.

2. The scattered radiation correction method according to claim 1, further comprising:
   estimating a primary X-ray image based on the projection images collected by the CT-like imaging and the initial estimation image of the scattered radiation images; and
   calculating a first scattered radiation estimation image based on the estimated primary X-ray image.

3. A scattered radiation correction method comprising:
   generating a reduced image for each of a plurality of projection images collected by CT-like imaging;
   identifying a first scattered radiation image on the basis of the reduced image;
   generating a second scattered radiation image by enlarging the first scatted radiation image; and
   subtracting the second scattered radiation image from each of the respective collection images, thereby correcting the scattered radiation.

4. The scattered radiation correction method according to claim 3, further comprising:
   when estimating to identify a scattered radiation image from a projection image in an arbitrary projection direction of a plurality of projection images collected by CT-like imaging, setting a first scattered radiation image in an adjacent projection direction which is already identified, as an initial estimation image of the first scattered radiation images.

5. The scattered radiation correction method according to claim 4, further comprising:
   estimating a primary X-ray image based on the reduced image of each of the projection images collected by the CT-like imaging and the initial estimation image of the scattered radiation images; and
   calculating a first scattered radiation estimation image based on the estimated primary X-ray image.

6. The scattered radiation correction method according to claim 3, the method comprising:
   when removing scattered radiation image from a plurality of projection images collected by CT-like imaging, estimating first and second scattered radiation images common in adjacent projection directions from θi to θj.

* * * * *